(12) United States Patent
Kuo

(10) Patent No.: US 10,195,482 B2
(45) Date of Patent: Feb. 5, 2019

(54) INTELLIGENT COURT SYSTEM AND A DATA THEREOF ACQUISITION METHOD

(71) Applicant: GENGEE TECHNOLOGY CO., LTD., Xiamen, Fujian (CN)

(72) Inventor: Daisung Kuo, Fujian (CN)

(73) Assignee: GENGEE TECHNOLOGY CO., LTD., Xiamen (CN)

( * ) Notice: Subject to any disclaimer, the term of this patent is extended or adjusted under 35 U.S.C. 154(b) by 0 days.

(21) Appl. No.: 15/737,135

(22) PCT Filed: Mar. 17, 2016

(86) PCT No.: PCT/CN2016/076613
§ 371 (c)(1),
(2) Date: Dec. 15, 2017

(87) PCT Pub. No.: WO2016/206412
PCT Pub. Date: Dec. 29, 2016

(65) Prior Publication Data
US 2018/0169472 A1    Jun. 21, 2018

(30) Foreign Application Priority Data

Jun. 25, 2015    (CN) .......................... 2015 1 0357351

(51) Int. Cl.
*A63B 24/00* (2006.01)
*A63B 71/06* (2006.01)
(52) U.S. Cl.
CPC .......... *A63B 24/0006* (2013.01); *A63B 71/06* (2013.01); *A63B 2024/0012* (2013.01)

(58) Field of Classification Search
CPC .................................................... A63B 63/083
See application file for complete search history.

(56) References Cited

U.S. PATENT DOCUMENTS

2009/0231198 A1* 9/2009 Walsh ................ A63B 24/0021
                                                            342/463
2011/0304497 A1* 12/2011 Molyneux ............ A43B 1/0054
                                                            342/42
2014/0361906 A1* 12/2014 Hughes .................... H04Q 9/00
                                                            340/870.01

FOREIGN PATENT DOCUMENTS

| CN | 203315701 U | 12/2013 |
| CN | 204290953 U | 4/2015 |
| CN | 204319705 U | 5/2015 |

(Continued)

*Primary Examiner* — Omkar Deodhar
(74) *Attorney, Agent, or Firm* — Rabin & Berdo, P.C.

(57) ABSTRACT

An intelligent court system and a data acquisition method includes an intelligent ball, a plurality of wearing devices, a plurality of location base stations, gateway and server, the location base stations, the gateway; the intelligent ball is disposed with a first UWB label; the wearing device is disposed with a second UWB label; the location base station is disposed with a UWB receiving and transporting device, a micro-controller, a clock device and a data communication device, the micro-controller controls the UWB receiving and transporting device to receive the information from the intelligent ball and the wearing device and adds a timestamp of a clock signal from the UWB receiving and transporting device, and then transports the information to the gateway via the data communication device; the server receives the information from the gateway to determine the position and/or the motion trail of the intelligent ball and/or the wearing device.

15 Claims, 8 Drawing Sheets

(56) References Cited

FOREIGN PATENT DOCUMENTS

| | | |
|---|---|---|
| CN | 204319729 U | 5/2015 |
| CN | 104722058 A | 6/2015 |
| CN | 105105755 A | 12/2015 |
| JP | 2002511593 A | 4/2002 |

\* cited by examiner

INTELLIGENT COURT SYSTEM AND A DATA THEREOF ACQUISITION METHOD

FIELD OF THE INVENTION

The present invention relates to intelligent sports system, particularly to an intelligent court system and a data thereof acquisition method.

BACKGROUND OF THE INVENTION

In recent years, intelligent device industry is developing rapidly. One main reason that the Intelligent devices are popular is the software application development and the publish ecosystem of intelligent devices. Hundreds of new applications come into the market to prompt the ecosystem to evolve. However, in the numbers of software applications, mainsteams are pure software applications and web application, the application of kinds of sensors (accelerometer, gyroscope, magnetometer, GPS, etc) in the intelligent devices are limited to maps and games.

In the existing technology, the intelligent devices can be applied in sports, for example, patent CN102779319A, the intelligent monitoring system is used in outdoor sports. But said intelligent system can only achieve information sharing, navigational positioning modules of every client in a local area network. The system is mainly applied for single or multiple sports persons.

For high strength and heavy load competitions like football, basketball or volleyball, the sports person needs to play high level of individual and collective tactic when running such to beat the opponents. Therefore, how to combine the high strength training load and the specific skill is the key to improve the specific ability of the sports persons.

SUMMARY OF THE INVENTION

The main object of the present invention is to provide with an intelligent court system and a data thereof acquisition method by acquiring relative motion data of the intelligent ball and the sports person so as to provide a data support for the improvement of the specific ability of the sports persons.

The technical proposal of the present invention is that:

An intelligent court system, comprising a plurality of wearing devices, a plurality of location base stations, gateway and server, the location base stations are arranged at different positions of the court, the location base stations are connected to the gateway by wire or wireless mode, the gateway is connected to the server by wire or wireless mode, wherein further comprising an intelligent ball, the intelligent ball is disposed with a first UWB label used to broadcast an identification code and motion information to the location base stations; the wearing device is disposed with a second UWB label used to broadcast an identification code and motion information to the location base stations; the location base station is disposed with a UWB receiving and transporting device, a micro-controller, a clock device and a data communication device, the micro-controller controls the UWB receiving and transporting device to receive the information from the intelligent ball and the wearing device and adds a timestamp of a clock signal from the UWB receiving and transporting device, and then transports the information to the gateway via the data communication device, the clock device is used to add a timestamp corresponding to other motion or sign data; the server receives the information from the gateway to determine the position and/or the motion trail of the intelligent ball and/or the wearing device.

In another preferred embodiment, the first UWB label comprises a first micro-control unit, a first six-axis inertial sensor, a first clock unit, a first storage device and a first UWB wireless receiving and transporting unit; the first six-axis inertial sensor is connected to the first micro-control unit to detect the motion information of the intelligent ball, the first lock unit is connected to the first micro-control unit to provide a clock signal corresponding to the inertial sensor data; the first storage device is connected to the first micro-control unit to temporally store the motion information; the first UWB wireless receiving and transporting unit builds a time signal source to broadcast and identification code and motion information such that the base station locates the first UWB wireless receiving and transporting unit after receiving the information.

In another preferred embodiment, the intelligent ball is further disposed with a battery device and a wireless charging receiving device, the wireless charging receiving device is connected to the battery device to wireless charge the battery device, the battery device is connected to the first UWB label to supply power.

In another preferred embodiment, the second UWB label comprises a second micro-control unit, a second six-axis inertial sensor, a second clock unit, a second storage device and a second UWB wireless receiving and transporting unit; the second six-axis inertial sensor is connected to the second micro-control unit to detect the motion information of the intelligent ball, the second lock unit is connected to the second micro-control unit to provide a clock signal corresponding to the inertial sensor data; the second storage device is connected to the second micro-control unit to temporally store the motion information; the second UWB wireless receiving and transporting unit builds a time signal source to broadcast and identification code and motion information such that the base station locates the second UWB wireless receiving and transporting unit after receiving the information.

In another preferred embodiment, the wearing device is further disposed with a battery device and a wireless charging receiving device, the wireless charging receiving device is connected to the battery device to wireless charge the battery device, the battery device is connected to the second UWB label and a body information acquisition device to supply power.

In another preferred embodiment, the wearing device is further disposed with a body information acquisition device, which is connected to the second UWB label to acquire physical information and transport to the location base stations.

In another preferred embodiment, the server acquires the motion information and the timestamp of the corresponding UWB wireless receiving and transporting unit via the received identification code of the intelligent ball or the wearing device, and determines the position of the intelligent ball or the wearing device according to the time of the timestamp comparison information reaching different base stations or the time difference, and combines the motion information to obtain the motion trail.

In another preferred embodiment, one location base station is set to transport time synchronous signal according to a preset period; the other location base stations, the intelligent ball and the wearing device adjust the built-in clock device of the corresponding UWB receiving and transporting device after receiving the time synchronous signal to maintain the time synchronization.

In another preferred embodiment, the broadcast order of the intelligent ball and the wearing devices is preset with a max idle time; the intelligent ball or the wearing device monitors other devices and waits to broadcast until the arrival of the broadcast order, and then resets the max idle time after the broadcasting.

In another preferred embodiment, the data communication device comprises at least one of a WiFi unit, a LAN unit, a 3G data unit, a 4G data unit or a USB interface.

A ball sports data acquisition method, wherein a first UWB label is assembled in a ball, a sports person wears a wearing device with a second UWB label and a body information acquisition device, a plurality of location base stations are arranged in a court, one location base station is set to transport time synchronous signal according to a preset period; the data acquisition method comprises the steps:

1) the ball or the wearing device determines whether received the time synchronous signal, if so, executing the time synchronization; if not, determining whether reaching the broadcast time slot or not, if so, the ball transports an identification code and a motion information via the first UWB label, the wearing device transports an identification code, a motion information and a performance information to the location base station via the second UWB label;
2) the location base station determines whether received the time synchronous signal, if so, executing the time synchronization; if not, the base station determines whether received the information from the ball or the wearing device, if so, adding a timestamp to the information and transporting the same to the server via the gateway;
3) the server calculates and determines the position and the motion trail of the intelligent ball and the wearing device.

In another preferred embodiment, in step 3), the server acquires the motion information and the timestamp of the corresponding UWB wireless receiving and transporting unit via the received identification code of the intelligent ball or the wearing device, and determines the position of the intelligent ball or the wearing device according to the time of the timestamp comparison information reaching different base stations or the time difference, and combines the motion information to obtain the motion trail.

In another preferred embodiment, the body information acquisition device acquires the body performance information, which comprises electrocardiography, heart rate, myoelectricity, pulse, blood oxygen, respiratory rate.

A ball sports data acquisition method, wherein a first UWB label is assembled in a ball, a sports person wears a wearing device with a second UWB label and a body information acquisition device, a plurality of location base stations are arranged in a court, one location base station is set to transport time synchronous signal according to a preset period, and the broadcast order of the intelligent ball and the wearing devices is preset with a max idle time; the data acquisition method comprises the steps:

1) the ball or the wearing device determines whether the max idle time reaches, if so, the ball transport an identification code and motion information after random delay, the wearing device broadcasts an identification code, a motion information and a body performance information to the location base station, then the max idle time is reset; if not, monitoring whether the previous broadcast order device finishes the broadcasting, if so, the ball transport an identification code and motion information, the wearing device broadcasts an identification code, a motion information and a body performance information to the location base station, then the max idle time is reset, if not, repeating the step;
2) the location base station determines whether received the time synchronous signal, if so, executing the time synchronization; if not, the base station determines whether received the information from the ball or the wearing device, if so, adding a timestamp to the information and transporting the same to the server via the gateway;
3) the server calculates and determines the position and the motion trail of the intelligent ball and the wearing device.

In another preferred embodiment, in step 3), the server acquires the motion information and the timestamp of the corresponding UWB wireless receiving and transporting unit via the received identification code of the intelligent ball or the wearing device, and determines the position of the intelligent ball or the wearing device according to the time of the timestamp comparison information reaching different base stations or the time difference, and combines the motion information to obtain the motion trail.

In another preferred embodiment, the body information acquisition device acquires the body performance information, which comprises electrocardiography, heart rate, myoelectricity, pulse, blood oxygen, respiratory rate.

Compared to the existing known technology, the present invention has advantages as follows:

The system and the method of the present invention are applied with an intelligent ball, wearing devices, location base stations and a server to precisely acquire the motion data of the intelligent ball and the sports person wearing the wearing device, the present invention achieves motion location and trail monitoring, the information can be served as the basis for data analysis and later training in a sports training or a competition, the user can use a mobile device, such as a phone, a notebook or a pad to download the training or competition data from the server.

DETAILED DESCRIPTION OF THE EMBODIMENTS

Figure 1:
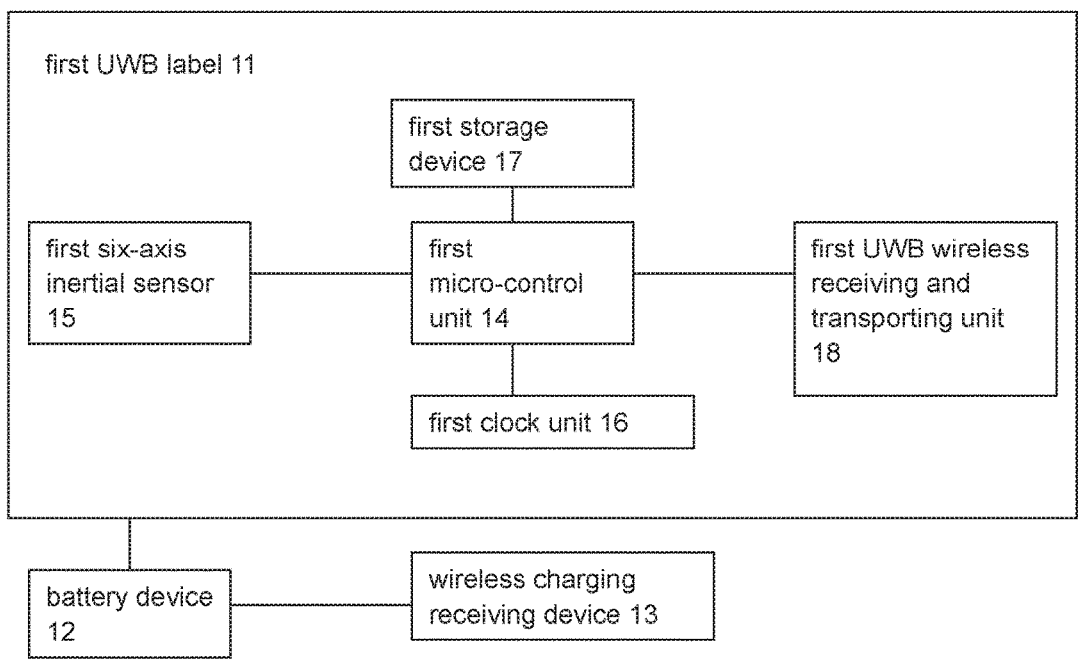
FIG. 1 illustrates a block diagram of the intelligent ball of the present invention.
Figure 2:
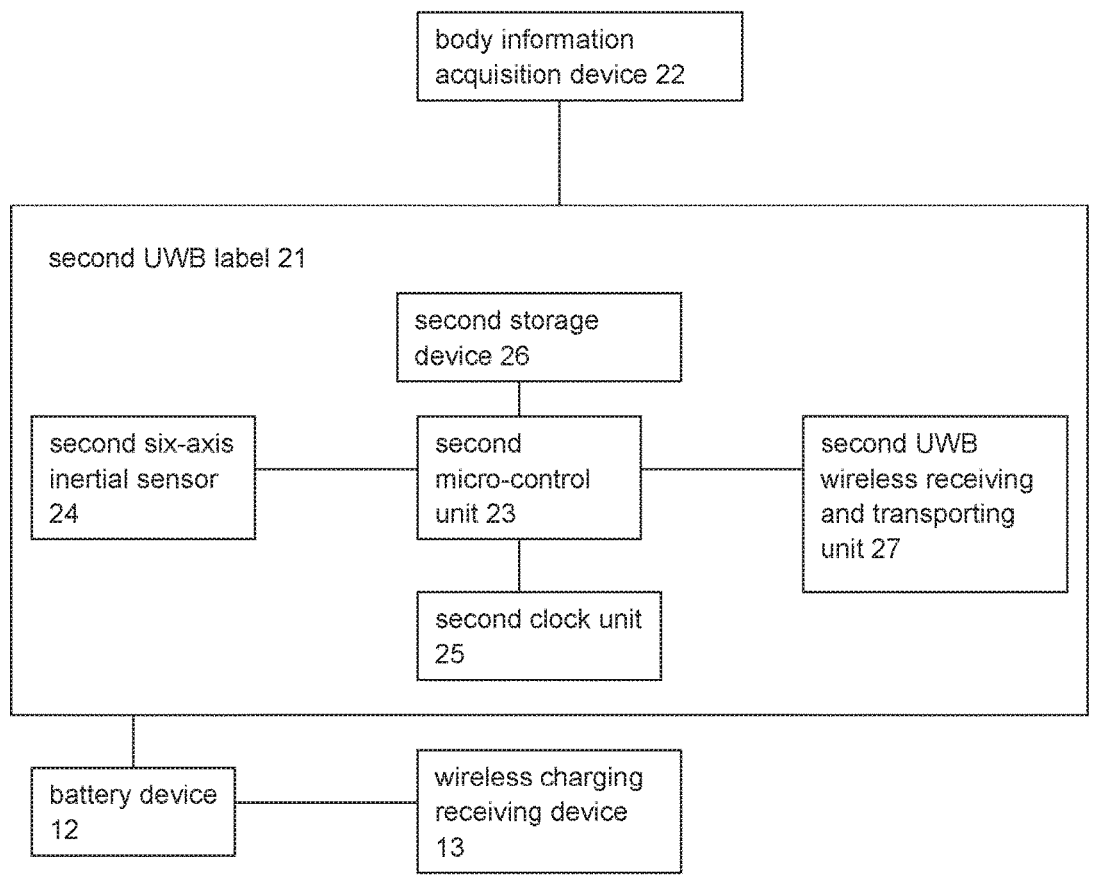
FIG. 2 illustrates a block diagram of the wearing device of the present invention.
Figure 3:
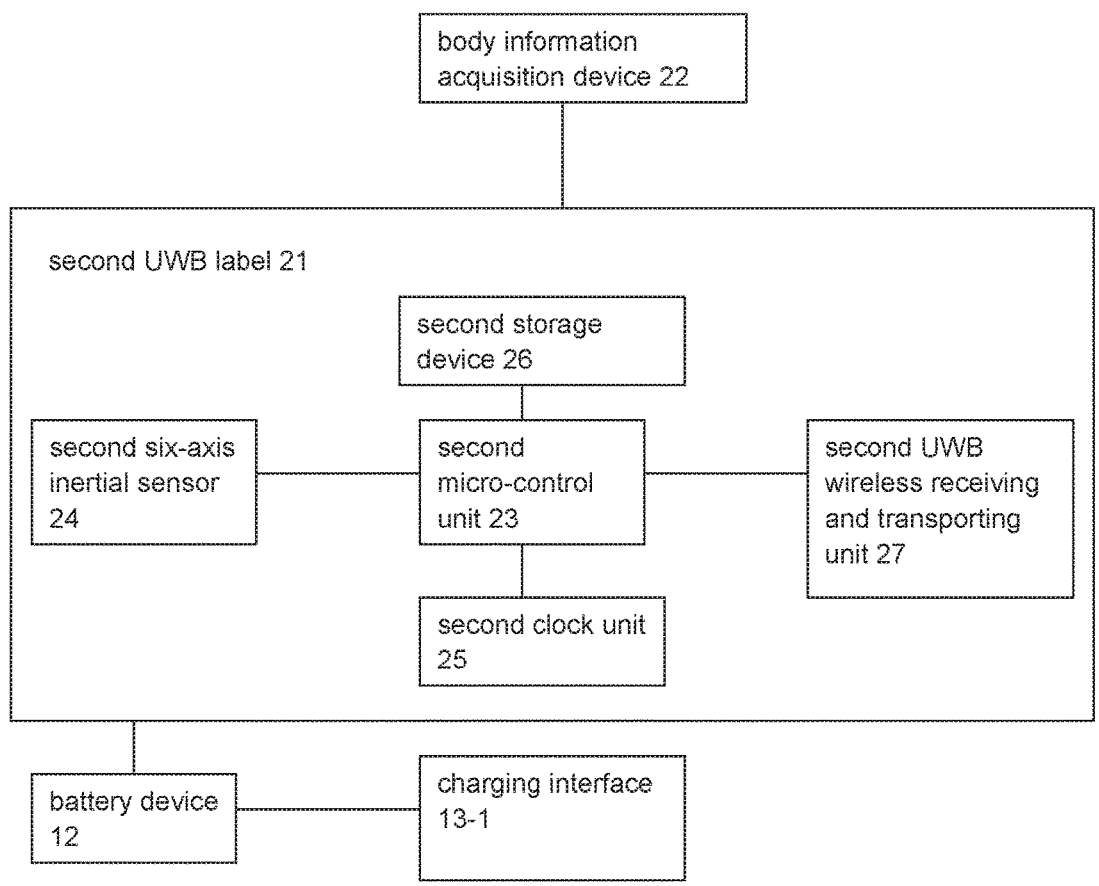
FIG. 3 illustrates a block diagram of the wearing device of the present invention with another charging mode.
Figure 4:
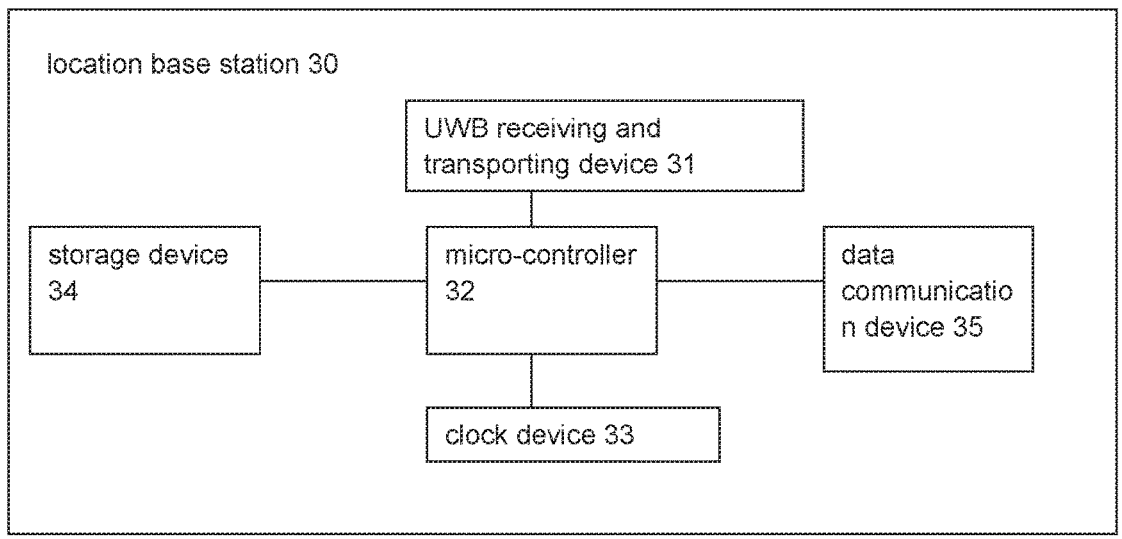
FIG. 4 illustrates a block diagram of the base station of the present invention.
Figure 5:
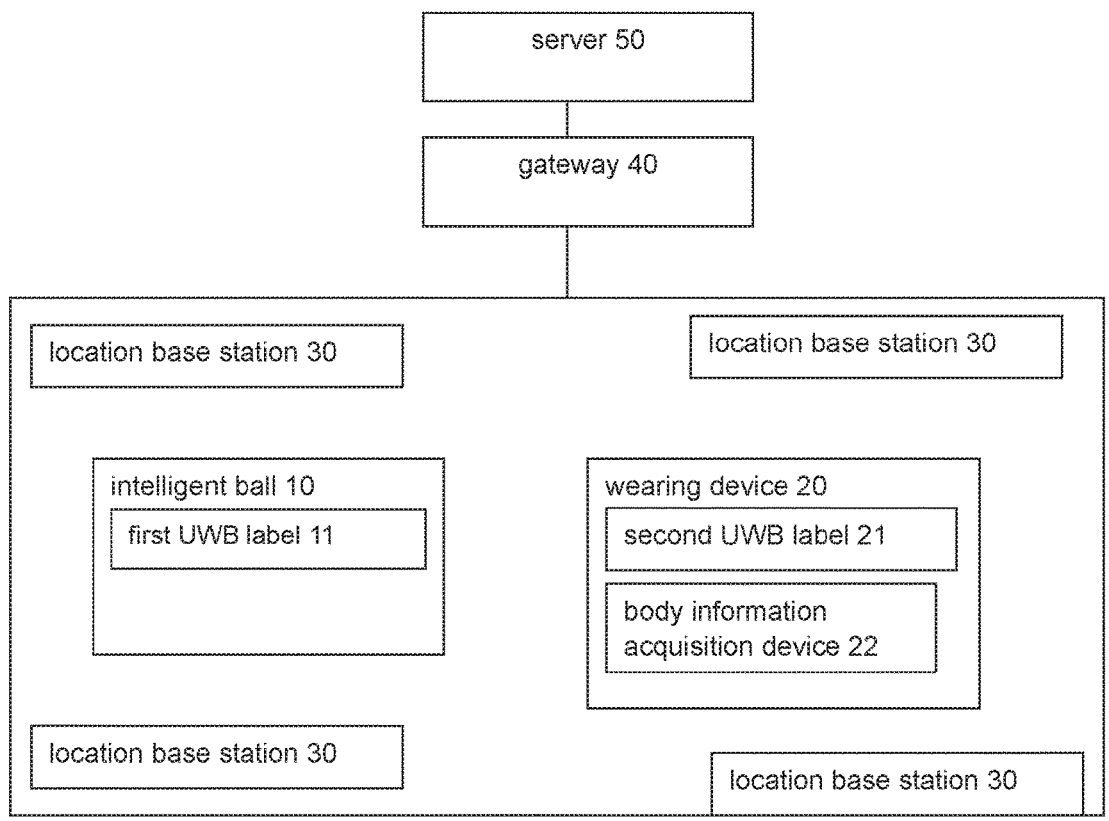
FIG. 5 illustrates a block diagram of the system of the present invention.

The present invention will be further described with the drawings and the embodiments.

Referring to FIGS. 1~5, an intelligent court system comprises an intelligent ball 10, a plurality of wearing devices 20, a plurality of location base stations 30, gateway 40 and server 50. The intelligent ball 10 is disposed with a first UWB label 11, a battery device 12 and a wireless charging receiving device 13. The wireless charging receiving device 13 is connected to the battery device 12 to wireless charge the battery device, the battery device 12 is connected to the first UWB label 11 to supply power. The first UWB label 11 comprises a first micro-control unit 14, a first six-axis inertial sensor 15, a first clock unit 16, a first storage device 17 and a first UWB wireless receiving and transporting unit 18; the first six-axis inertial sensor 15 is connected to the first micro-control unit 14 to detect the motion information of the intelligent ball 10, the motion information comprises acceleration variate and angular velocity variate, such to achieve trial compensation of the location spots of the intelligent ball 10; the first lock unit 16 is connected to the first micro-control unit 14 to provide a clock signal corresponding to the inertial sensor data; the first storage device 17 is connected to the first micro-control unit 14 to temporally store the motion information; the first UWB wireless receiving and transporting unit 18 is used to broadcast an identification code and a motion information, the first micro-control unit 14 controls each component to work.

The wearing device 20 is assembled with a second UWB label 21, a body information acquisition device 22, a battery device 12 and a wireless charging receiving device 13; the wireless charging receiving device 13 is connected to the battery device 12 to wireless charge the battery device, the battery device 12 is connected to the second UWB label 21 and the body information acquisition device 22 to supply power. The body information acquisition device 22 is connected to the second UWB label 21 to acquire the body performance information, which comprises electrocardiography, heart rate, myoelectricity, pulse, blood oxygen, respiratory rate. The second UWB label 21 comprises a second micro-control unit 23, a second six-axis inertial sensor 24, a second clock unit 25, a second storage device 26 and a second UWB wireless receiving and transporting unit 27; the second six-axis inertial sensor 24 is connected to the second micro-control unit 25 to detect the motion information of the intelligent ball 10, the motion information comprises acceleration variate and angular velocity variate, such to achieve trial compensation of the location spots of the wearing device 20; the second lock unit 25 is connected to the second micro-control unit 23 to provide a clock signal corresponding to the inertial sensor data and body performance data; the second storage device 26 is connected to the second micro-control unit 23 to temporally store the motion information; the second UWB wireless receiving and transporting unit 27 is used to broadcast an identification code, a motion information and a body performance information; the second micro-control unit 23 controls each component to work.

The location base stations 30 are arranged at different positions of the court, the location base station 30 is disposed with a UWB receiving and transporting device 31, a micro-controller 32, a clock device 33, a storage device 34 and a data communication device 35; the micro-controller 32 controls the UWB receiving and transporting device 31 to receive the information from the intelligent ball 10 and the wearing device 20 and adds a timestamp of a clock signal from the UWB receiving and transporting device 31 and the clock device 33, and then transports the information to the gateway 40 via the data communication device 35. The location base station 30 is connected to the gateway 40 by wire or wireless mode. The number of the location base stations 30 can be three, forming a plane with X-axis and Y-axis, the UWB receiving and transporting device 31 is disposed in the plane; four or more location base stations 30 are available, forming a 3D space with X-axis, Y-axis, Z-axis, the UWB receiving and transporting device 31 is disposed in the space. The data communication device comprises at least one of a WiFi unit, a LAN unit, a 3G data unit, a 4G data unit or a USB interface, to serve as the connecting passage to the server 50. In addition, one location base station 30 is set to transport time synchronous signal according to a preset period; the other location base stations 30 adjust the built-in clock device of the corresponding UWB receiving and transporting device 31 after receiving the time synchronous signal to maintain the time synchronization. The intelligent ball 10 and the wearing device 20 adjust the UWB receiving and transporting device 31 and the clock device 33 after received the time synchronous signal of the specific location base station 30 to maintain the time synchronization.

The gateway 40 is connected to the server 50 by wire or wireless mode. The server 50 receives the information (comprising the performance information form the wearing device 20) from the gateway 40 and calculates the position and motion trail of the intelligent ball 10 and the wearing devices 20 by time difference location method (TDOA, TOA or TOF location method). In detailed, the server 50 acquires the motion information and the timestamp of the corresponding UWB wireless receiving and transporting unit via the received the identification code of the intelligent ball 10 or the wearing device 20, and determines the position of the intelligent ball 10 or the wearing device 20 according to the time of the timestamp comparison information reaching different base stations 30 or the time difference, and combines the motion information to obtain the motion trail. The server 50 can be a local server or a cloud server to analyze the position and time relationship of the intelligent ball 10 and the wearing device 20 by comparison and to further provide varies of data, for example, for a football, it can provide holding time, passing success rate, score statistic, number of time of attempt interruption and number of time of interruption.

Figure 6:
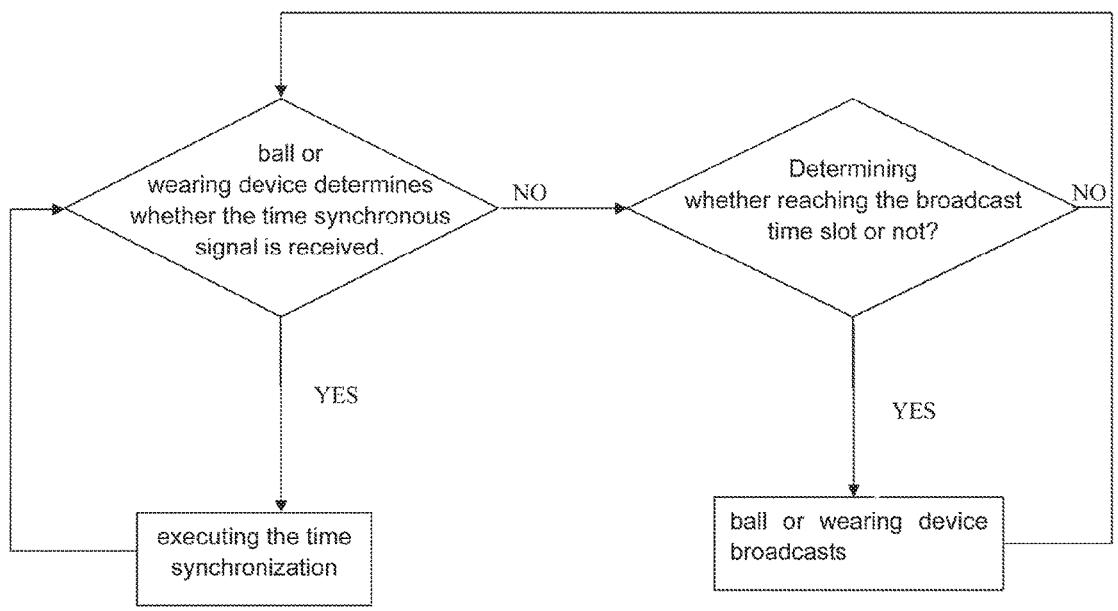
FIG. 6 illustrates a flow diagram of the ball or the wearing device of the method of the present invention.
Figure 7:
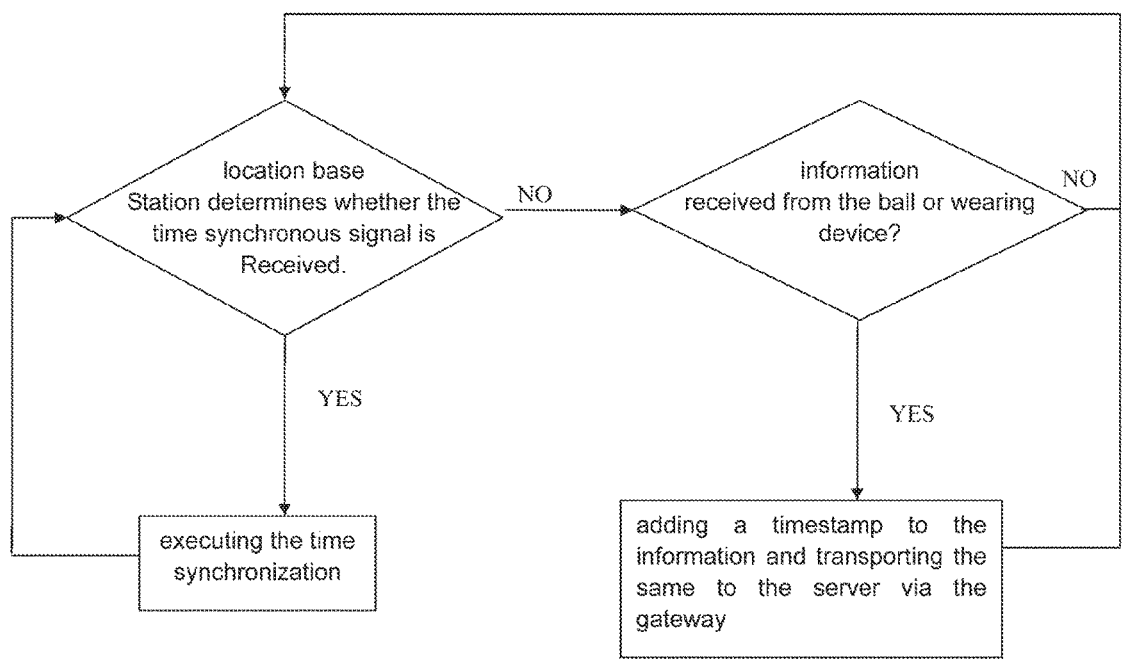
FIG. 7 illustrates a work flow diagram of the location base stations of the method of the present invention, except the base station used to transport time synchronous signal.

Based on the system, the present invention is provided with a ball sports data acquisition method, wherein a first UWB label 11 is assembled in a ball, a sports person wears a wearing device 20 with a second UWB label 21 and a body information acquisition device 22, a plurality of location base stations 30 are arranged in a court, one location base station 30 is set to transport time synchronous signal according to a preset period, the ball and the wearing devices are disposed with broadcast time slot; referring to FIG. 6 and FIG. 7, the data acquisition method comprises the steps:

1) the ball or the wearing device 20 determines whether received the time synchronous signal, if so, executing the time synchronization; if not, determining whether reaching the broadcast time slot or not, if so, the ball transports an identification code and a motion information via the first UWB label 11, the wearing device 20 transports an identification code, a motion information and a performance information to the location base station 30 via the second UWB label 21;

2) the location base station 30 determines whether received the time synchronous signal, if so, executing the time synchronization; if not, the base station determines whether received the information from the ball or the wearing device 20, if so, adding a timestamp to the information and transporting the same to the server 50 via the gateway 50. For the location base station 30 used to transport time synchronous signal, it determines whether having transporting the time synchronous signal, if not, transporting the time synchronous signal; if so, determining whether having received the information from the ball or the wearing device 20, if so, adding a timestamp to the information and transporting the same to the server 50 via the gateway 50.

3) the server 50 calculates and determines the position and the motion trail of the intelligent ball 10 and the wearing device 20 by time difference location method. In detailed, the server 50 acquires the motion information and the timestamp via the received identification code of the intelligent ball 10 or the wearing device 20, and determines the position of the intelligent ball 10 or the wearing device 20 according to the time of the timestamp of the UWB wireless receiving and transporting unit comparison information reaching different base stations or the time difference, and combines the motion information to obtain the motion trail.

Figure 8:
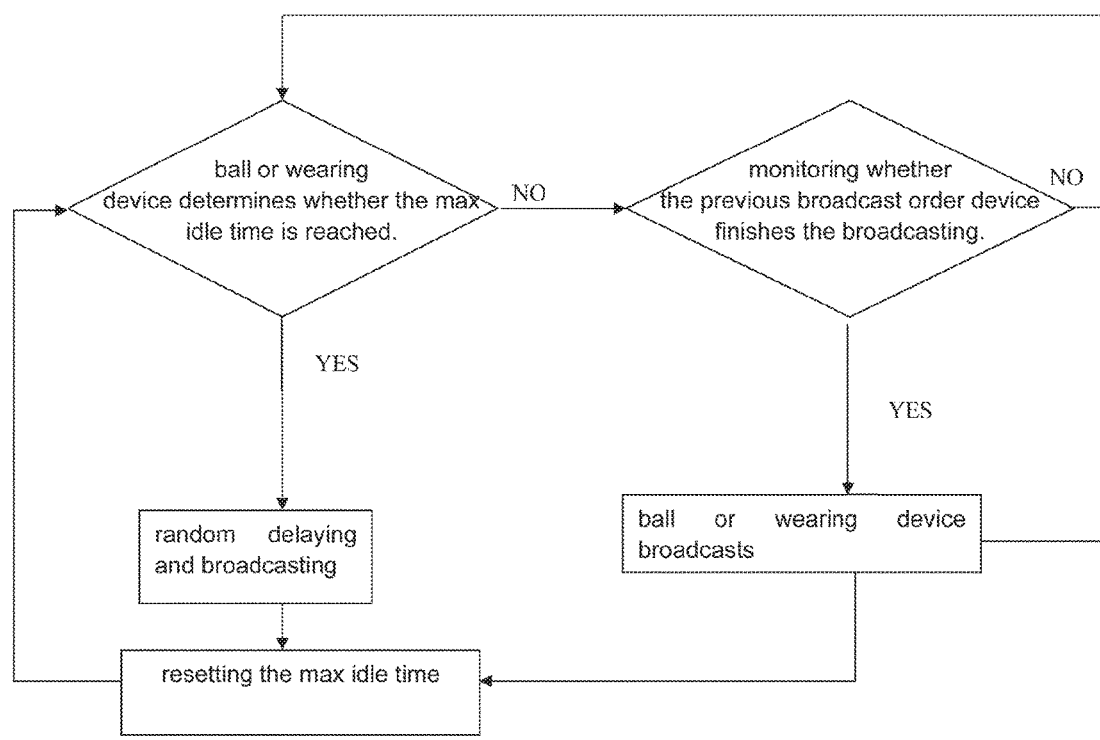
FIG. 8 illustrates a work flow diagram of the ball or the wearing device of the method of the present invention in another working mode.

Another ball sports data acquisition method of the present invention is provided that the intelligent ball 10 and the wearing devices 20 can not be in time synchronization. In detailed, a first UWB label 11 is assembled in a ball, a sports person wears a wearing device with a second UWB label 21 and a body information acquisition device 22, a plurality of location base stations 30 are arranged in a court, one location base station 30 is set to transport time synchronous signal according to a preset period, and the broadcast order of the intelligent ball 10 and the wearing devices 20 is preset with a max idle time; referring to FIG. 8 and FIG. 7, the data acquisition method comprises the steps:

1) the ball or the wearing device determines whether the max idle time reaches, if so, the ball transport an identification code and motion information after random delay (random delay means the data is transported via wireless by unfixed time method to prevent data collusion), the ball broadcast an identification code and a motion information, the wearing device 20 broadcasts an identification code, a motion information and a body performance information to the location base station 30, then the max idle time is reset to avoid that data can not be transported if the previous order of information doesn't reach; if not, monitoring whether the previous broadcast order device finishes the broadcasting, if so, the ball transport an identification code and motion information, the wearing device 20 broadcasts an identification code, a motion information and a body performance information to the location base station, 30 then the max idle time is reset, if not, repeating the step. A timer can be used to achieve timing of the max idle time.

2) the location base station 30 determines whether received the time synchronous signal, if so, executing the time synchronization; if not, the base station determines whether received the information from the ball or the wearing device 20, if so, adding a timestamp to the information and transporting the same to the server 50 via the gateway 50. For the location base station 30 used to transport time synchronous signal, it determines whether having transporting the time synchronous signal, if not, transporting the time synchronous signal; if so, determining whether having received the information from the ball or the wearing device 20, if so, adding a timestamp to the information and transporting the same to the server 50 via the gateway 50.

3) the server 50 calculates and determines the position and the motion trail of the intelligent ball 10 and the wearing device 20 by time difference location method. In detailed, the server 50 acquires the motion information and the timestamp via the received identification code of the intelligent ball 10 or the wearing device 20, and determines the position of the intelligent ball 10 or the wearing device 20 according to the time of the timestamp of the UWB wireless receiving and transporting unit comparison information reaching different base stations or the time difference, and combines the motion information to obtain the motion trail.

In the method of the present invention, the server 50 can be a local sever or a cloud server, which can precisely determine the position and the motion trail of the intelligent ball and the sports person wearing the wearing device, the present invention achieves motion location and trail monitoring, the information can be served as the basis for data analysis and later training. the user can use a mobile device, such as a phone, a notebook or a pad to download the training or competition data from the server.

Although the present invention has been described with reference to the preferred embodiments thereof for carrying out the patent for invention, it is apparent to those skilled in the art that a variety of modifications and changes may be made without departing from the scope of the patent for invention which is intended to be defined by the appended claims.

INDUSTRIAL APPLICABILITY

The present invention is provided with an intelligent court system and a data thereof acquisition method, which can precisely acquire the motion data of the intelligent ball and the sports person wearing the wearing device, the information can be served as the basis for data analysis and later training in a sports training or a competition.

The invention claimed is:

1. An intelligent court system, comprising a plurality of wearing devices, a plurality of location base stations, gateway and server,
   wherein the location base stations are arranged at different positions of the court, the location base stations are connected to the gateway by wire or wireless mode, the gateway is connected to the server by wire or wireless mode,
   wherein the intelligent court system further comprises an intelligent ball, the intelligent ball is disposed with a first UWB label used to broadcast an identification code and motion information to the location base stations; the wearing device is disposed with a second UWB label used to broadcast an identification code and motion information to the location base stations; a location base station is disposed with a UWB receiving and transporting device, a micro-controller, a clock device and a data communication device, the micro-controller controls the UWB receiving and transporting device to receive the information from the intelligent ball and the wearing device and adds a timestamp of a clock signal from the UWB receiving and transporting device, and then transports the information to the gateway via the data communication device, the clock device is used to add a timestamp corresponding to other motion or sign data; the server receives the information from the gateway to determine a position and/or a motion trail of the intelligent ball and/or the wearing device; and
   wherein the intelligent ball is further disposed with a battery device and a wireless charging receiving device, the wireless charging receiving device is connected to the battery device to wirelessly charge the battery device, the battery device is connected to the first UWB label to supply power.

2. The intelligent court system according to claim 1, wherein the first UWB label comprises a first micro-control unit, a first six-axis inertial sensor, a first clock unit, a first storage device and a first UWB wireless receiving and transporting unit; the first six-axis inertial sensor is connected to the first micro-control unit to detect the motion information of the intelligent ball, the first clock unit is connected to the first micro-control unit to provide a clock signal corresponding to inertial sensor data; the first storage device is connected to the first micro-control unit to temporally store the motion information; the first UWB wireless receiving and transporting unit builds a time signal source to broadcast an identification code and motion information such that the base station locates the first UWB wireless receiving and transporting unit after receiving the information.

3. The intelligent court system according to claim 1, wherein the second UWB label comprises a second micro-control unit, a second six-axis inertial sensor, a second clock unit, a second storage device and a second UWB wireless receiving and transporting unit; the second six-axis inertial sensor is connected to the second micro-control unit to detect the motion information of the intelligent ball, the second clock unit is connected to the second micro-control unit to provide a clock signal corresponding to the inertial sensor data; the second storage device is connected to the second micro-control unit to temporally store the motion information; the second UWB wireless receiving and transporting unit builds a time signal source to broadcast an identification code and motion information such that the base station locates the second UWB wireless receiving and transporting unit after receiving the information.

4. The intelligent court system according to claim 1, wherein the wearing device is further disposed with a battery device and a wireless charging receiving device, the wireless charging receiving device is connected to the battery device to wirelessly charge the battery device, the battery device is connected to the second UWB label and a body information acquisition device to supply power.

5. The intelligent court system according to claim 1, wherein the wearing device is further disposed with a body information acquisition device, which is connected to the second UWB label to acquire and transport physical information to the location base stations.

6. The intelligent court system according to claim 1, wherein the server acquires motion information and a timestamp of a corresponding UWB wireless receiving and transporting unit via a received identification code of the intelligent ball or the wearing device, and determines the position of the intelligent ball or the wearing device according to timestamp comparison information reaching different base stations or a time difference, and combines the motion information to obtain the motion trail.

7. The intelligent court system according to claim 1, wherein one location base station is set to transport a time synchronous signal according to a preset period; other location base stations, the intelligent ball and the wearing device adjust a built-in clock device of a corresponding UWB receiving and transporting device after receiving the time synchronous signal to maintain time synchronization.

8. The intelligent court system according to claim 1, wherein a broadcast order of the intelligent ball and the wearing device is preset with a max idle time; the intelligent ball or the wearing device monitors other devices and waits to broadcast until arrival of the broadcast order, and then resets the max idle time after the broadcasting.

9. The intelligent court system according to claim 1, wherein the data communication device comprises at least one of a WiFi unit, a LAN unit, a 3G data unit, a 4G data unit or a USB interface.

10. A ball sports data acquisition method, wherein a first UWB label is assembled in a ball, a sports person wears a wearing device with a second UWB label and a body information acquisition device, a plurality of location base stations are arranged in a court, one location base station is set to transport a time synchronous signal according to a preset period;

the data acquisition method comprises the steps:
1) the ball or the wearing device determines whether the time synchronous signal is received, if so, executing time synchronization; if not, determining whether a broadcast time slot is reached, if so, the ball transports an identification code and motion information via the first UWB label, the wearing device transports an identification code, the motion information and performance information to the location base station via the second UWB label;
2) the location base station determines whether the time synchronous signal is received, if so, executing the time synchronization; if not, the base station determines whether information is received from the ball or the wearing device, if so, adding a timestamp to the information and transporting the information to a server via a gateway;
3) the server calculates and determines a position and a motion trail of the intelligent ball and the wearing device.

11. The ball sports data acquisition method according to claim 10, wherein in step 3), the server acquires the motion information and the timestamp of a corresponding UWB wireless receiving and transporting unit via a received identification code of the intelligent ball or the wearing device, and determines the position of the intelligent ball or the wearing device according to timestamp comparison information reaching different base stations or a time difference, and combines the motion information to obtain the motion trail.

12. The ball sports data acquisition method according to claim 10, wherein the body information acquisition device acquires body performance information, which comprises electrocardiography, heart rate, myoelectricity, pulse, blood oxygen, respiratory rate.

13. A ball sports data acquisition method, wherein a first UWB label is assembled in a ball, a sports person wears a wearing device with a second UWB label and a body information acquisition device, a plurality of location base stations are arranged in a court, one location base station is set to transport a time synchronous signal according to a preset period, and a broadcast order of the intelligent ball and the wearing device is preset with a max idle time; the data acquisition method comprises the steps:
1) the ball or the wearing device determines whether the max idle time is reached, if so, the ball transports an identification code and ball motion information after a random delay, the wearing device broadcasts another identification code, wearing device motion information and body performance information to the location base station, then the max idle time is reset; if not, monitoring whether a previous broadcast order device finishes the broadcasting, if so, the ball transports the identification code and ball motion information, the wearing device broadcasts the other identification code, the wearing device motion information and the body performance information to the location base station, then the max idle time is reset, if not, repeating the step;
2) the location base station determines whether the time synchronous signal is received, if so, executing time synchronization; if not, the base station determines whether information is received from the ball or the wearing device, if so, adding a timestamp to the information and transporting the information to a server via a gateway;

3) the server calculates and determines a position and a motion trail of the intelligent ball and the wearing device.

14. The ball sports data acquisition method according to claim 13, wherein in step 3), the server acquires motion information and a timestamp of a corresponding UWB wireless receiving and transporting unit via a received identification code of the intelligent ball or the wearing device, and determines the position of the intelligent ball or the wearing device according to the timestamp comparison information reaching different base stations or a time difference, and combines the motion information to obtain the motion trail.

15. The ball sports data acquisition method according to claim 13, wherein the body information acquisition device acquires the body performance information, which comprises electrocardiography, heart rate, myoelectricity, pulse, blood oxygen, respiratory rate.

\* \* \* \* \*